(12) United States Patent
Suenari et al.

(10) Patent No.: US 12,085,582 B2
(45) Date of Patent: Sep. 10, 2024

(54) AUTOMATIC ANALYSIS DEVICE, AUTOMATIC ANALYSIS SYSTEM, AND AUTOMATIC ANALYSIS METHOD FOR ANALYTES

(71) Applicant: HITACHI HIGH-TECH CORPORATION, Tokyo (JP)

(72) Inventors: Tsukasa Suenari, Tokyo (JP); Masashi Akutsu, Tokyo (JP); Hiroyuki Mishima, Tokyo (JP); Takeshi Setomaru, Tokyo (JP); Akihiro Yasui, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 804 days.

(21) Appl. No.: 17/284,763

(22) PCT Filed: Dec. 2, 2019

(86) PCT No.: PCT/JP2019/047053
§ 371 (c)(1),
(2) Date: Apr. 12, 2021

(87) PCT Pub. No.: WO2020/149033
PCT Pub. Date: Jul. 23, 2020

(65) Prior Publication Data
US 2021/0389337 A1 Dec. 16, 2021

(30) Foreign Application Priority Data

Jan. 18, 2019 (JP) ................................. 2019-006630

(51) Int. Cl.
| | | |
|---|---|---|
| *G01N 33/53* | (2006.01) | |
| *G01N 35/00* | (2006.01) | |
| *G01N 35/02* | (2006.01) | |

(52) U.S. Cl.
CPC ..... *G01N 35/0092* (2013.01); *G01N 33/5302* (2013.01); *G01N 35/02* (2013.01)

(58) Field of Classification Search
CPC . G01N 35/0092; G01N 33/5302; G01N 35/02
See application file for complete search history.

(56) References Cited

U.S. PATENT DOCUMENTS

2005/0123446 A1 6/2005 Yamazaki et al.

FOREIGN PATENT DOCUMENTS

| JP | 05-164763 A | 6/1993 |
|---|---|---|
| JP | 2005-164508 A | 6/2005 |

(Continued)

OTHER PUBLICATIONS

International Search Report, PCT/JP2019/047053, Dec. 24, 2019.

*Primary Examiner* — Jill A Warden
*Assistant Examiner* — Michael Stanley Gzybowski
(74) *Attorney, Agent, or Firm* — Volpe Koenig

(57) ABSTRACT

The present invention comprises: an incubator disk 22 upon which a plurality of reaction containers holding a reaction solution being an analyte and a reagent that have been mixed and reacted are mounted; a immunoassay unit 23 that measures the physical properties of the reaction solution; and a planning unit 103 that determines the order for measurement of analyte requested to be executed by the immunoassay unit 23. Measurement by the immunoassay unit 23 includes items having different measurement times. When measurement of sequence items having the longest measurement time will occur at least a prescribed number of times in a row, said prescribed number being at least two, the planning unit 103 provides at least one empty cycle after measurement has occurred at least the prescribed number of times.

6 Claims, 17 Drawing Sheets

(56) References Cited

FOREIGN PATENT DOCUMENTS

| | | |
|---|---|---|
| JP | 2010-181197 A | 8/2010 |
| JP | 2016-090536 A | 5/2016 |
| WO | 2008/050396 A1 | 5/2008 |

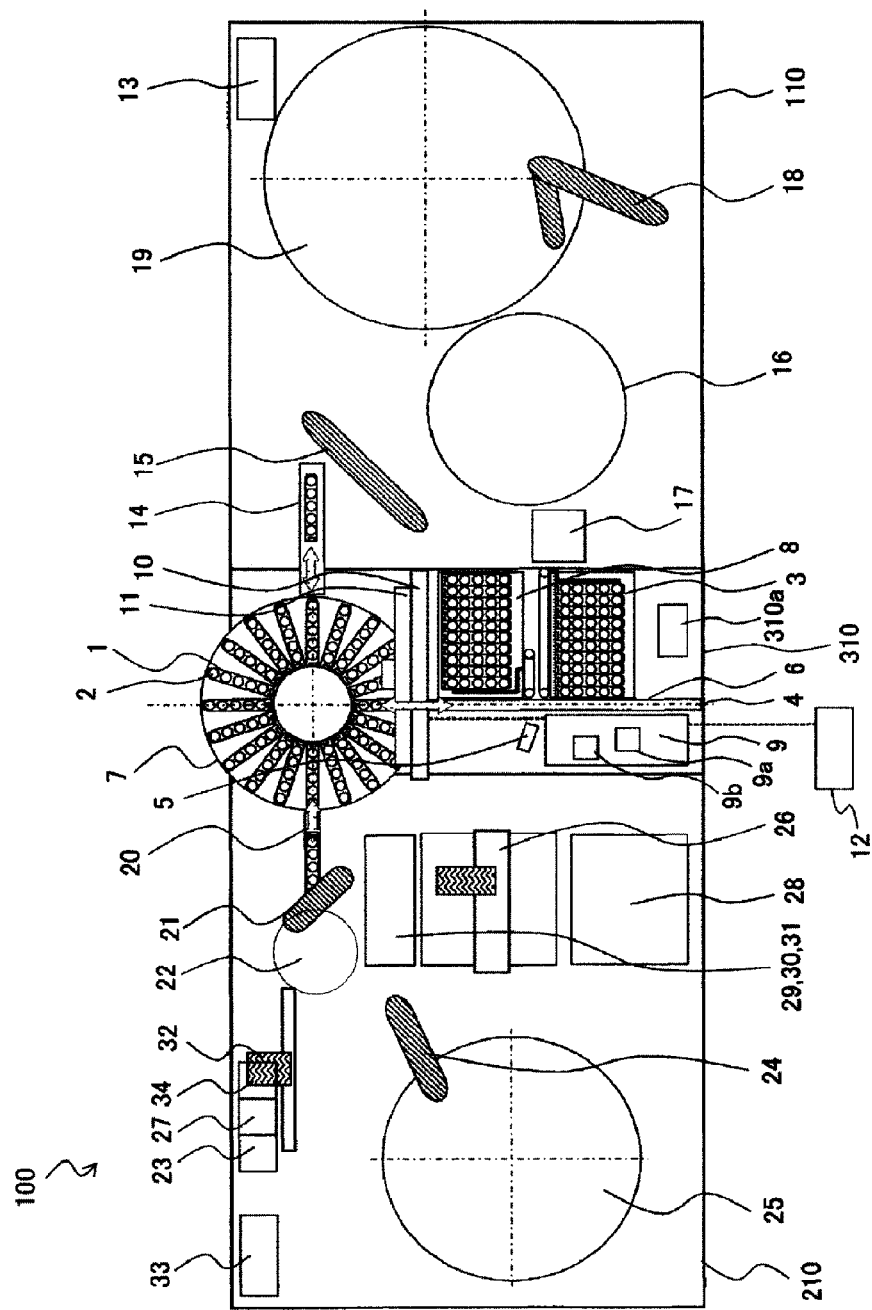
[FIG. 1]

[FIG. 2]
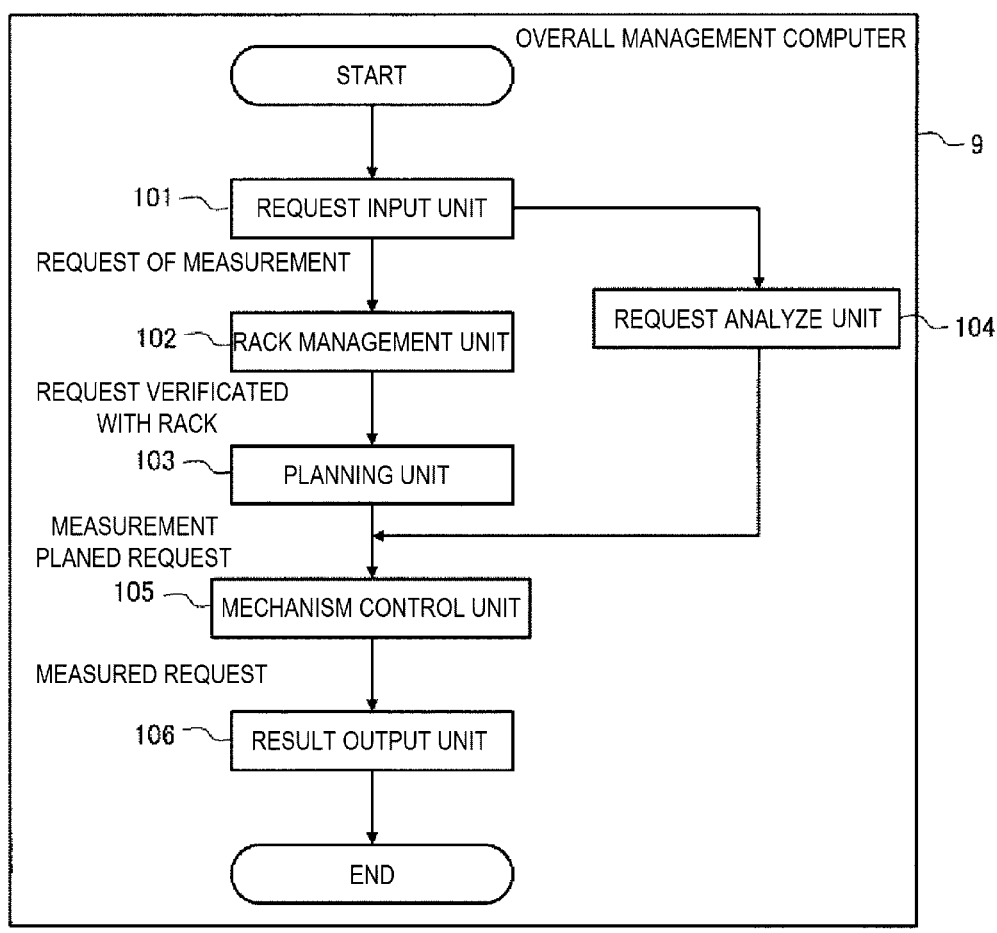

[FIG. 3]
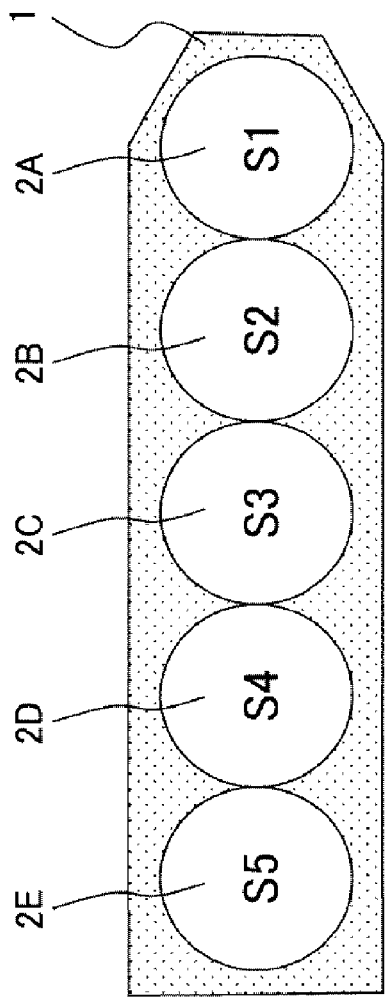

[FIG. 4]

| RACK TRANSPORT | DISPENSE |
|---|---|
| (1) TRANSPORT TO BIOCHEMICAL MODULE | S1(C1, C2, C3), S4(C1, C3), S5(C2, C3) |
| (2) TRANSPORT TO IMMUNE MODULE | S2(E1, E2$^H$), S3(E2$^H$), S5(E1) |
| (3) TRANSPORT AGAIN TO BIOCHEMICAL MODULE | S2(C1), S3(C1) |

[FIG. 5]

| RACK TRANSPORT | DISPENSE |
|---|---|
| (1) TRANSPORT TO IMMUNE MODULE | S2(E1, E2$^H$), S3(E2$^H$), S5(E1) |
| (2) TRANSPORT TO BIOCHEMICAL MODULE | S1(C1, C2, C3), S2(C1), S3(C1), S4(C1, C3), S5(C2, C3) |

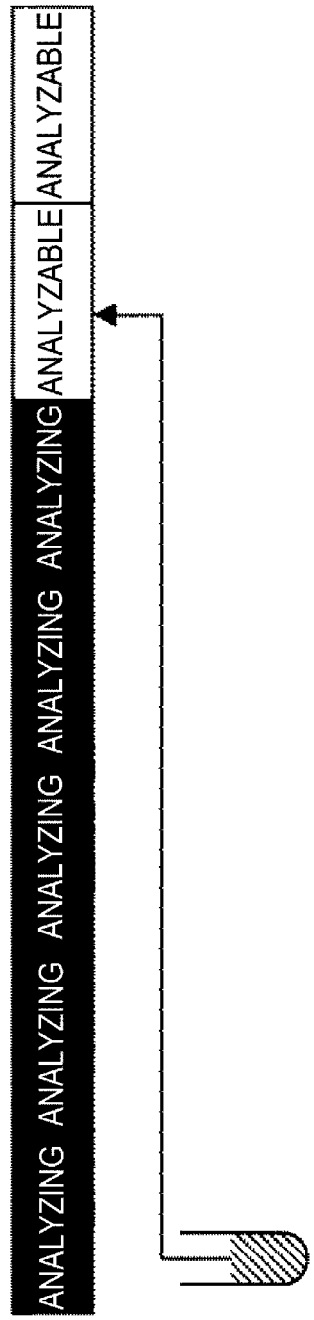
[FIG. 6]

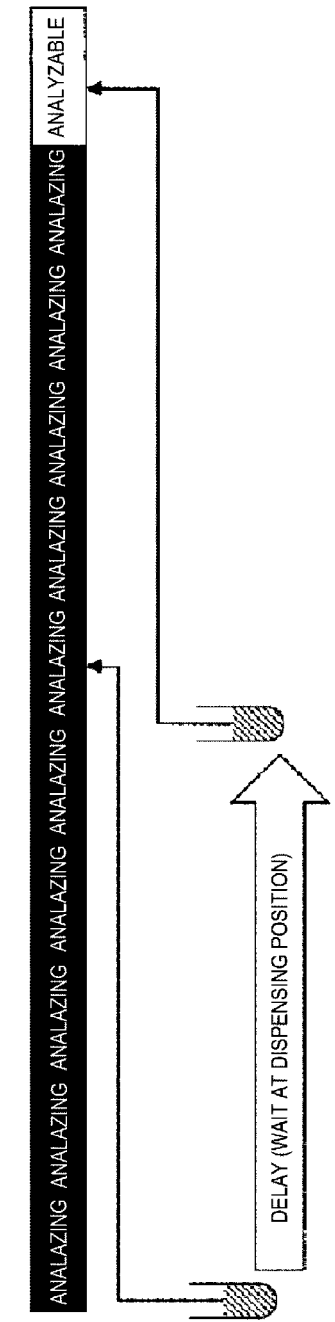
[FIG. 7]

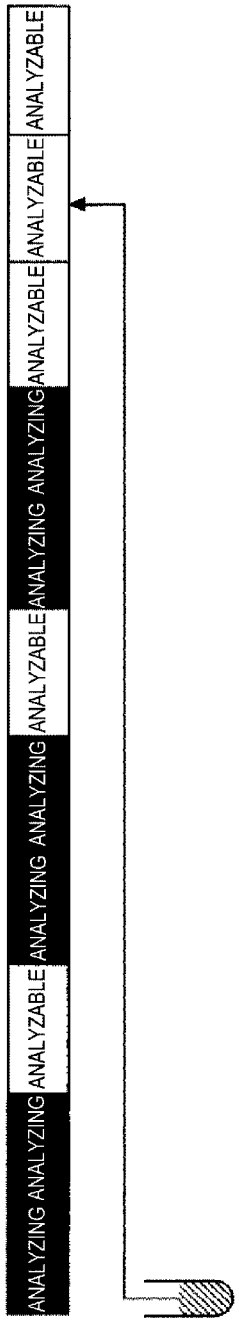
[FIG. 8]

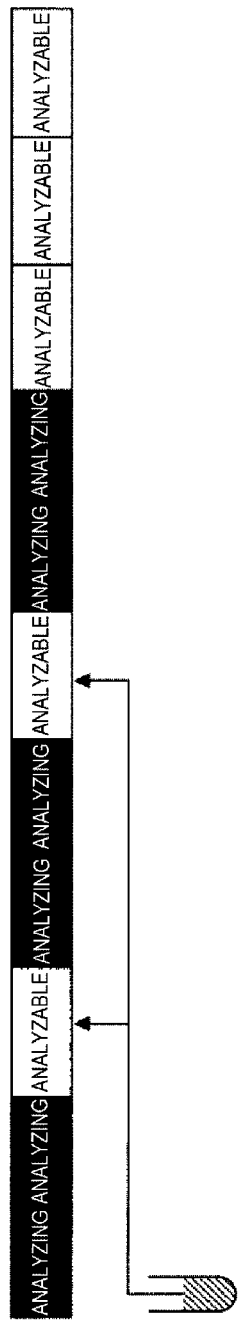
[FIG. 9]

[FIG. 10]

| TEST TUBE NUMBER | ANALYSIS NUMBER / 1 TEST TUBE | ANALYSIS ITEM | BIOCHEMICAL ANALYSIS TIMES | IMMUNE ANALYSIS TIMES |
|---|---|---|---|---|
| 50 | 3 | 10 MINUTES BIOCHEMICAL ANALYSIS | 150 | - |
|  | 1 | ISE (Na, K, Cl) ANALYSIS | 150 | - |
|  | 1 | 18 MINUTES IMMUNE ANALYSIS | - | 50 |

[FIG. 11]

| TEST TUBE NUMBER | ANALYSIS NUMBER / 1 TEST TUBE | ANALYSIS ITEM | BIOCHEMICAL ANALYSIS TIMES | IMMUNE ANALYSIS TIMES |
|---|---|---|---|---|
| 1 | 14 | 10 MINUTES BIOCHEMICAL ANALYSIS | 14 | - |
| | 1 | ISE (Na, K, Cl) ANALYSIS | 3 | |
| | 2 | 9 MINUTES IMMUNE ANALYSIS | - | 2 |

[FIG. 12]
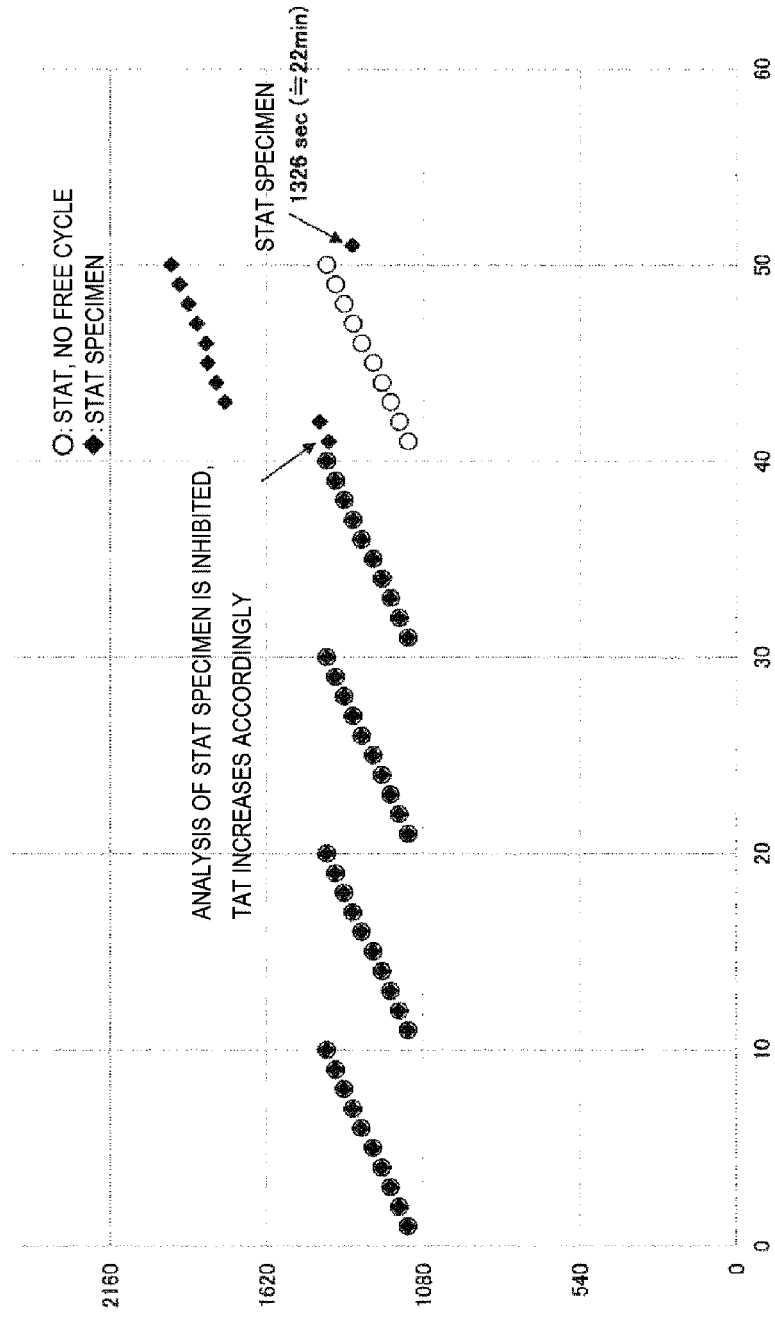

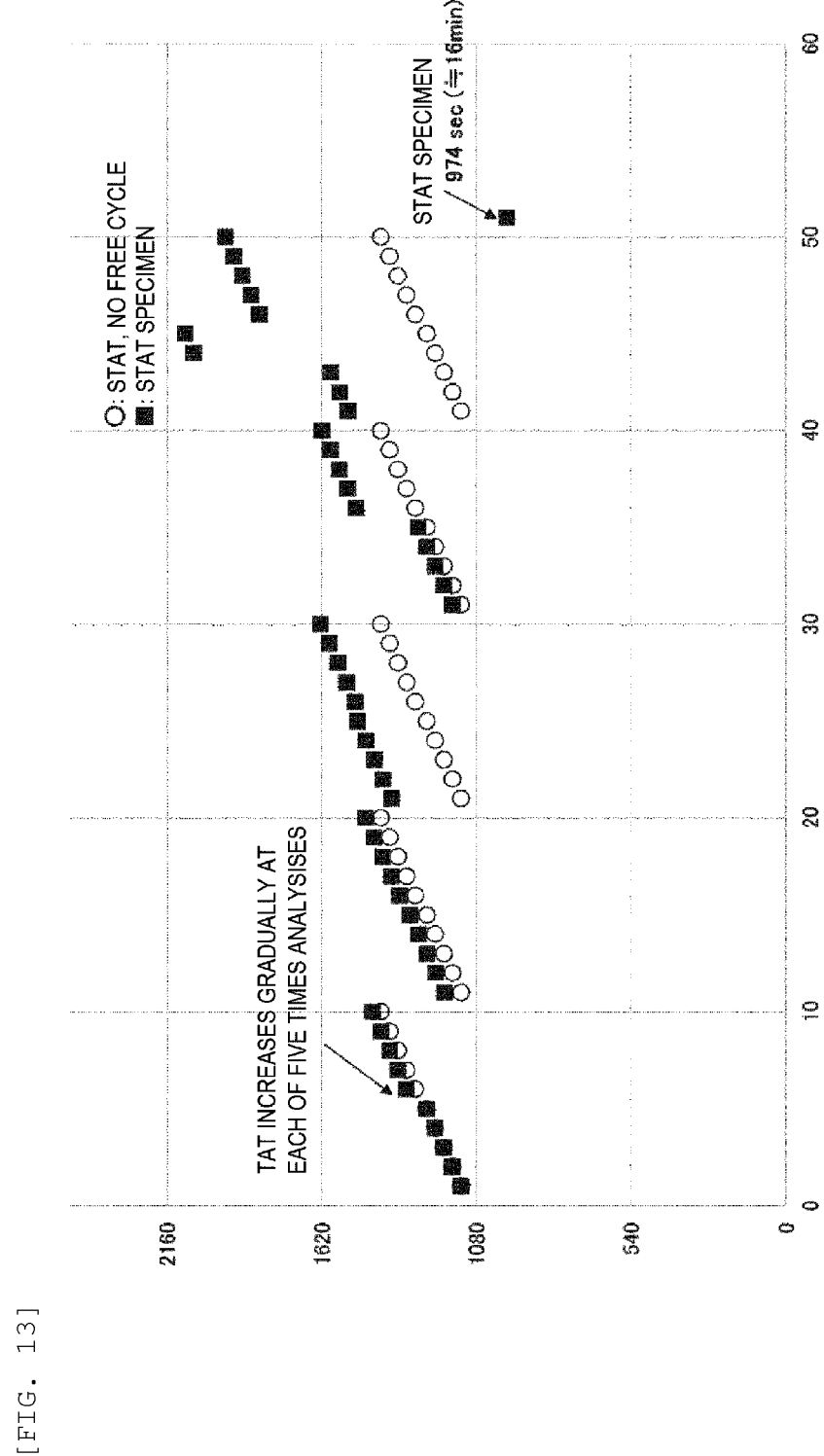
[FIG. 13]

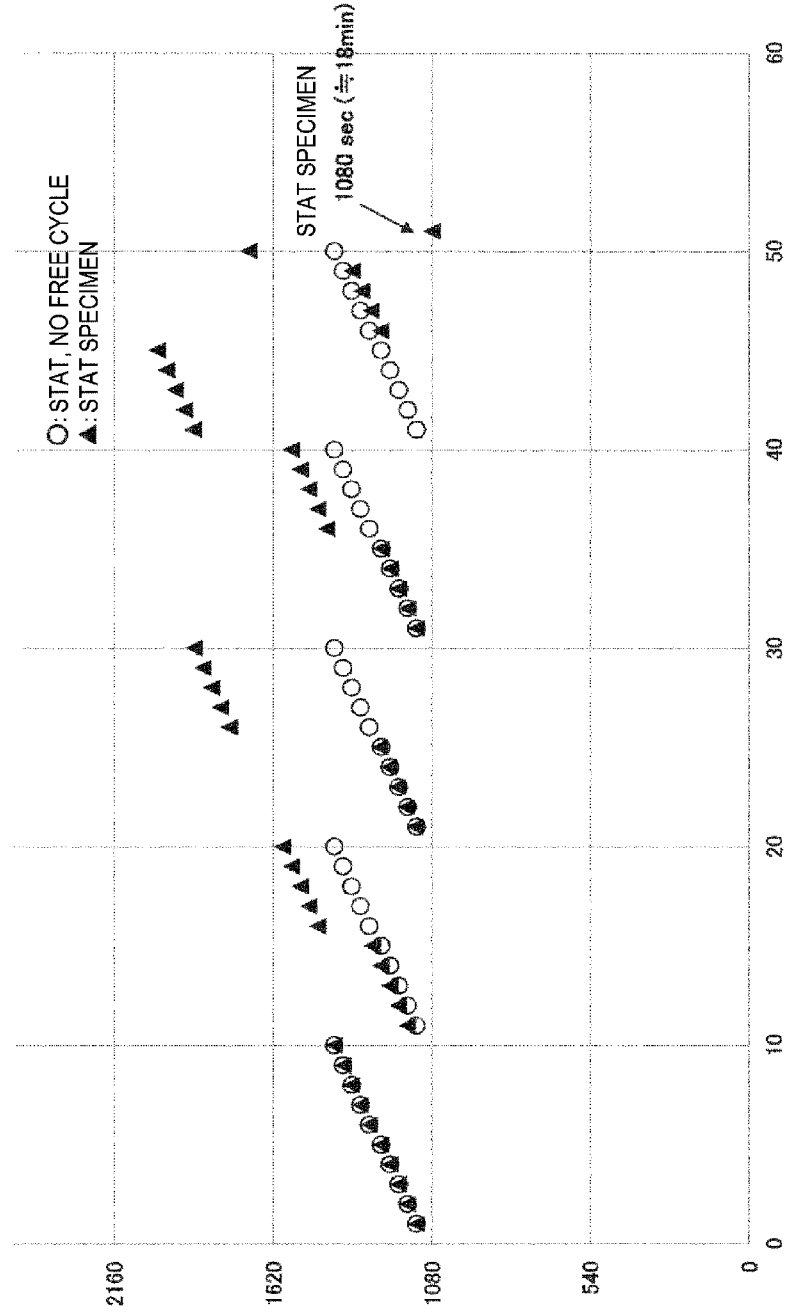
[FIG. 14]

[FIG. 15]
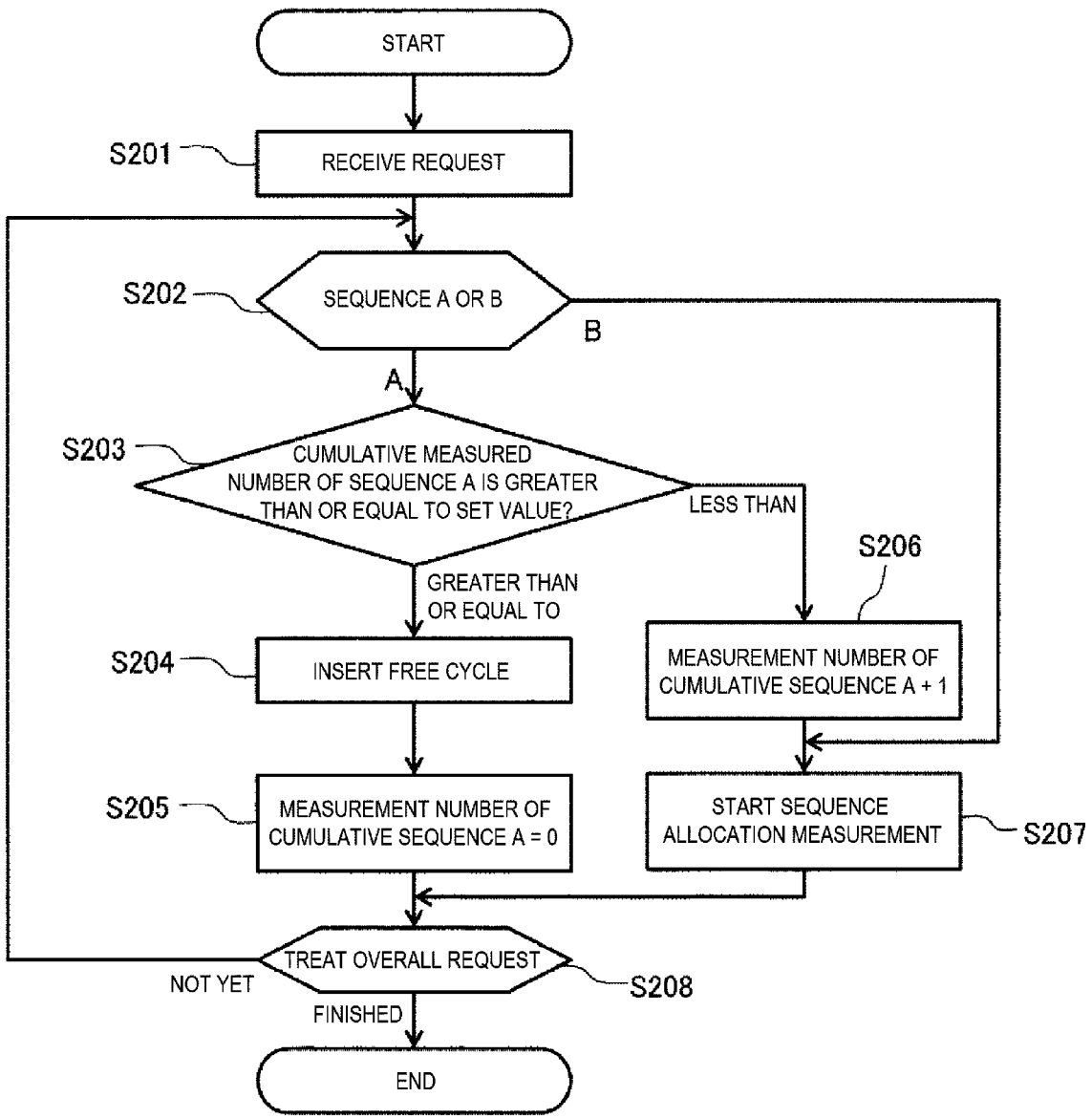

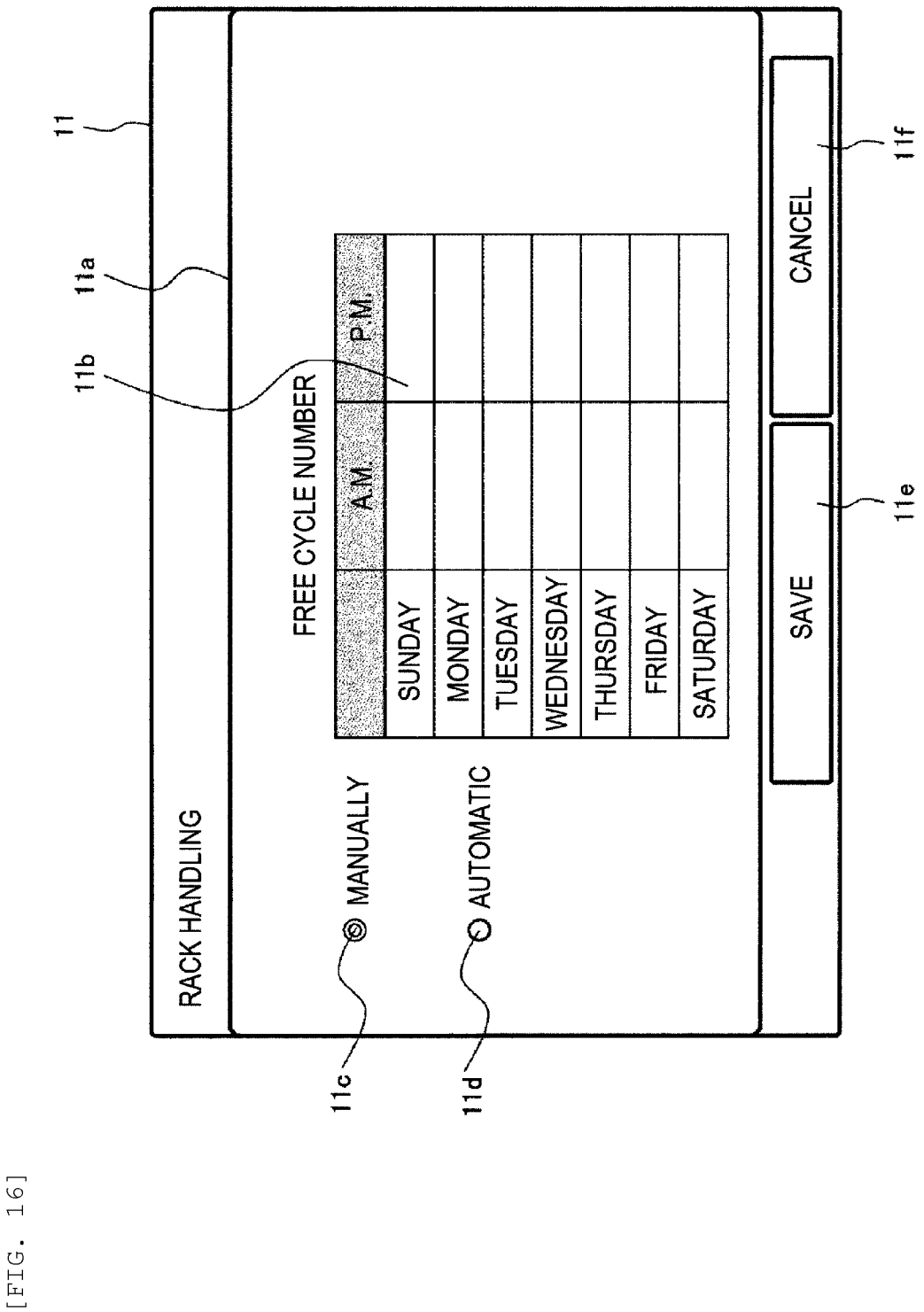
[FIG. 16]

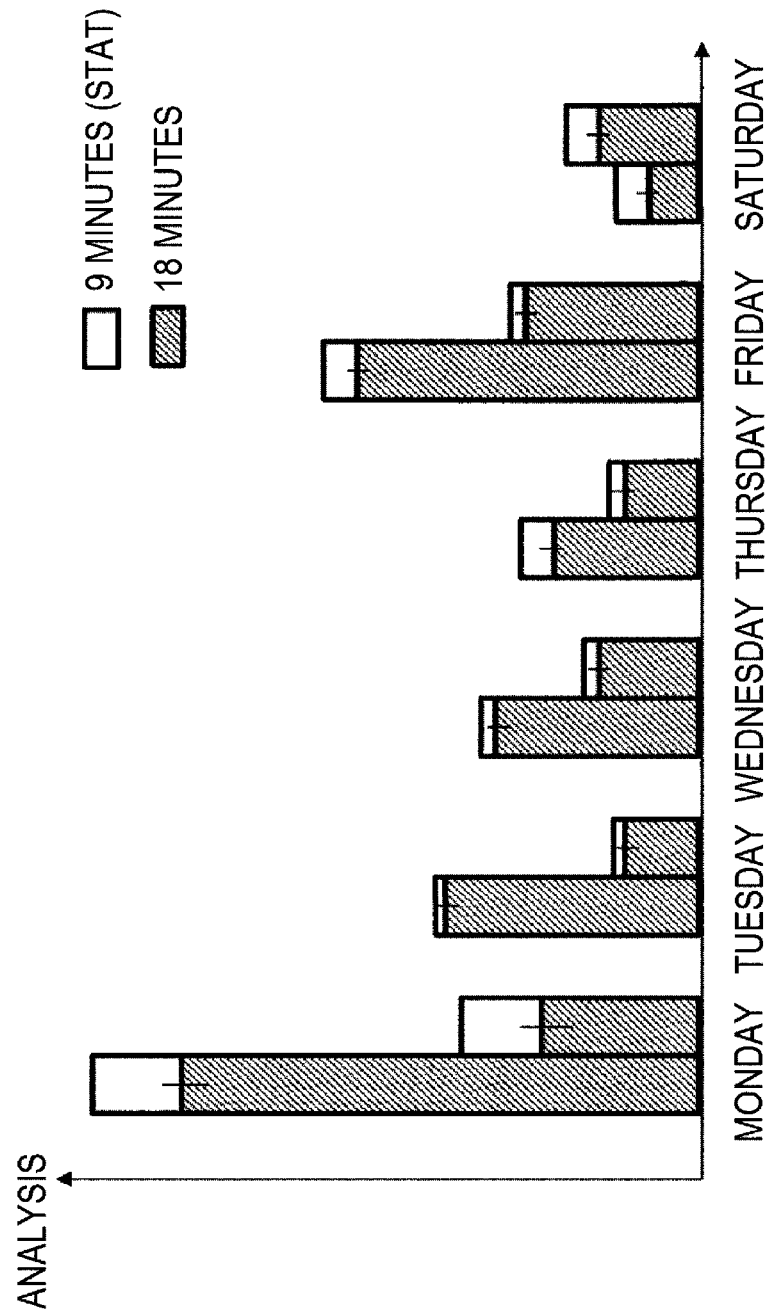
[FIG. 17]

AUTOMATIC ANALYSIS DEVICE, AUTOMATIC ANALYSIS SYSTEM, AND AUTOMATIC ANALYSIS METHOD FOR ANALYTES

TECHNICAL FIELD

The present invention relates to an automatic analyze device and an automatic analyze system for analyzing components in a biological sample (hereinafter referred to as a specimen) such as blood and urine, and an automatic analyze method for a specimen.

BACKGROUND ART

As an example of an automatic analyze device in which photometric time of a reaction detection tube can be set freely, a degree of freedom in device configuration can be increased, and an optimal arrangement can be performed, PTL 1 describes a device that measures a plurality of reaction detection tubes disposed on a circumference while moving the plurality of reaction detection tubes in an analysis cycle and performing sample dispensing, reagent dispensing, and reaction detection tube cleaning, in which when the number of reaction detection tubes is N and the number of reaction detection tubes that move in an analysis cycle is M, $N\pm1=A\times M$ (A is an integer of 2 or more), or there is no common factor other than 1 between N and M and $M<N/2$.

CITATION LIST

Patent Literature

PTL 1: JP-A-5-164763

SUMMARY OF INVENTION

Technical Problem

An automatic analyze device that analyzes a specimen using a reagent adopts a measurement method that differs depending on an item of a component to be measured. For example, there is an automatic biochemical analyze device that uses an analysis method (colorimetric analysis) using a reagent that changes the color of a reaction solution by reacting with a component to be analyzed in the specimen and an automatic immunological analyze device that uses an analysis method (immunological analysis) for counting a label by using a reagent in which the label is added to a substance to be bound specifically, directly or indirectly with the component to be analyzed.

For example, the automatic immunological analyze device has a measurement sequence including a series of operations such as specimen sampling, addition of reagent, stirring, incubation, and measurement of electrical signals in order to analyze a target component in a specimen.

In an automatic analyze device, it is common to sequentially analyze a plurality of inspection items in parallel by shifting a start timing of the measurement sequence by a fixed time and discretely starting the measurement sequence. PTL 1 discloses an example of such an automatic analyze device.

There is usually one type of sequence for one type of the automatic analyze device.

In the related art, there is also a technique of measuring a plurality of items requiring different reagent addition timings and reaction times (incubation times), which is also a method in which a maximum number of the reagent addition timings and a maximum reaction time is secured and a part of the reagent addition timings and the reaction times is omitted as necessary. Therefore, the measurement sequence of the same pattern is basically repeated.

Here, in the automatic analyze device, an emergency analysis item (hereinafter, sometimes referred to as a STAT item) that requires a short reaction time is an analysis item used for emergency specimen measurement or the like and usually requires a short turnaround time.

In particular, in a system in which a biochemical analyze device and an immunological analyze device are integrated, as for which device the rack is transported to when a specimen with both biochemical and immunological analysis items specified is held in a rack, and it is common to first transport the rack to an analyze device having a lighter load calculated based on loads of the analysis items (test time×the number of test items).

In a schedule of the biochemical analyze device, a reaction cell sequentially turns to sample dispensing, reagent dispensing, stirring, and spectrophotometer. Therefore, there is only one type of measurement sequence, and scheduling can be performed by adjusting the dispensing timing as a reference.

On the other hand, in a device configuration in which the immunological analyze device includes only one measurement unit (detector), when an 18-minute measurement sequence (A) that requires a long reaction time and a 9-minute measurement sequence (B) that requires a short reaction time are mixed, scheduling is performed centering on the measurement unit. This is because measurement time is longer than operation times of other mechanical parts. Therefore, when the measurement sequence (A) is continuously measured, the schedule of the measurement sequence (B) is established 9 minutes later, and waits at a dispensing position for 9 minutes.

As a result, even when it is determined that the immunological analyze device has a small load and the rack is first transported to the immunological analyze device, the rack may wait at the dispensing position of the immunological analyze device and time until the rack is transported to the biochemical analyze device may be extended, making the turnaround time deteriorate.

In contrast, even under a condition that the rack is first transported to the biochemical analyze device, dispensing is first necessary for the immunological device under a condition that there is an item with a high priority in an immunological analysis item.

Here, "high priority" is a flag given when it is necessary to perform dispensing first to avoid a situation in which a specimen amount is too small to execute analysis, and is given to an item that takes priority over dispensing for other analysis items.

Therefore, a flow is adopted in which another specimen is once dispensed in the biochemical analyze device and then in the immunological analyze device, and then the rack is transported to the biochemical analyze device again to dispense a high-priority specimen. However, the turnaround time of the specimen that has the measurement sequence B after the measurement sequence A is continuously performed deteriorates with biochemical items included.

Accordingly, even in a measurement sequence in which a measurement result can be obtained in a reaction of 9 minutes, the turnaround time may be 18 minutes, which is a problem to be solved.

In view of the above-described problems, the invention provides an automatic analyze device and an automatic analyze system capable of preventing fair deterioration in turnaround time of measurement even when items having different measurement sequences are mixed, and an automatic analyze method for a specimen.

Solution to Problem

The invention includes a plurality of systems that solves the above problems and provides an example thereof. An automatic analyze system which analyzes a specimen includes: at least two automatic analyze devices which are individually connected to two or more transport devices and analyze measurement items which are different from each other; and a transport device which supplies the specimen to the automatic analyze devices. Each of the automatic analyze devices includes: an incubator which is equipped with a plurality of reaction containers which hold reaction solution obtained by mixing and reacting the specimen with a reagent; a detection unit which measures a physical property of the reaction solution; and a planning unit which determines an order of a measurement of the specimen requested to be executed on the detection unit. The measurement in the detection unit includes items with different measurement times. The planning unit provides at least one free cycle after the measurement of at least a predetermined number of times which is at least two, when continuously measuring an item of a sequence with the longest measurement time for at least the predetermined number of times. The specimen is preferentially transported to the automatic analyze device on a side with a light load obtained by multiplying measurement time by a number of measurement items among the two or more sets of the automatic analyze devices, and when the measurement item in the plurality of automatic analyze devices on the same specimen is requested, a waiting time is long at a dispensing position in the automatic analyze device on the side with the light load, and when dispensing in the other automatic analyze device of the same specimen is delayed, the specimen is transported to the other automatic analyze device first regardless of the load.

Advantageous Effect

According to the invention, it is possible to prevent fair deterioration in turnaround time of measurement even when items having different measurement sequences are mixed. Problems, configurations, and effects other than those described above will be further clarified with the following description of embodiments.

BRIEF DESCRIPTION OF DRAWINGS

FIG. 1 is an explanatory view illustrating a module configuration of an automatic analyze system according to an embodiment of the present invention.

FIG. 2 is a diagram showing a partial function block and a processing flow of an overall management computer in the automatic analyze system according to the embodiment.

FIG. 3 is a view illustrating an outline of a specimen rack in the automatic analyze system according to the embodiment.

FIG. 4 is an explanatory diagram showing an example of a rack transport destination for an analyze request item in the automatic analyze system according to the embodiment.

FIG. 5 is an explanatory diagram showing an example of the rack transport destination for the analyze request item in the automatic analyze system according to the embodiment.

FIG. 6 is a diagram showing a dispensing timing when an item of a sequence with a short reaction time is measured after an item of a sequence with a long reaction time is measured continuously in a related automatic analyze system.

FIG. 7 is a diagram showing the dispensing timing when the item of the sequence with the short reaction time is measured after the item of the sequence with the long reaction time is measured continuously in the related automatic analyze system.

FIG. 8 is a diagram showing a dispensing timing when an item of a sequence with a long reaction time is measured after an item of a sequence with the long reaction time is measured continuously in the automatic analyze system according to the embodiment.

FIG. 9 is a diagram showing the dispensing timing when the item of a sequence with a short reaction time is measured after the item of the sequence with the long reaction time is measured continuously in the automatic analyze system according to the embodiment.

FIG. 10 is a diagram showing a setting of a request item of a general specimen out of conditions for verification of a turnaround time in a STAT (urgent) specimen in the automatic analyze system according to the embodiment.

FIG. 11 is a diagram showing a setting of the request item of the STAT specimen out of the conditions for the verification of the turnaround time in the STAT specimen in the automatic analyze system according to the embodiment.

FIG. 12 is a comparison diagram showing an example of the turnaround time when the STAT specimen is present in the related automatic analyze system for comparison with the automatic analyze system according to the embodiment.

FIG. 13 is a comparison diagram showing an example of the turnaround time when the STAT specimen is present when a free cycle is set once every five times in the automatic analyze system according to the embodiment.

FIG. 14 is a comparison diagram showing an example of the turnaround time when the STAT specimen is present when a free cycle is set once every ten times in the automatic analyze system according to the embodiment.

FIG. 15 is a flowchart showing processing of a planning unit of the overall management computer in the automatic analyze system according to the embodiment.

FIG. 16 is a screen of an example of a method of setting a schedule for the free cycle in the automatic analyze system according to the embodiment.

FIG. 17 is a diagram showing about a method of automatically calculating the setting of the free cycle in the automatic analyze system according to the embodiment.

DESCRIPTION OF EMBODIMENTS

Embodiments of an automatic analyze device, an automatic analyze system, and an automatic analyze method for a specimen of the invention will be described with reference to FIGS. 1 to 17.

First, an overall configuration of the automatic analyze system will be described with reference to FIG. 1. FIG. 1 is a diagram showing the overall configuration of the automatic analyze system according to the present embodiment.

An automatic analyze system 100 shown in FIG. 1 includes a transport module 310, a biochemical module 110 and an immune module 210 for analyzing a specimen, and an overall management computer 9.

The transport module 310 is a device that supplies a specimen container containing a specimen to the biochemical module 110 and the immune module 210, and includes a specimen rack input unit 3, an emergency specimen container input unit 4, a specimen and rack ID read unit 5, a transport line 6, a specimen rack waiting disk 7, a specimen rack housing unit 8, and a control unit for transport module 310a.

The biochemical module 110 and the immune module 210 are connected to both sides of the transport module 310 via the specimen rack waiting disk 7.

FIG. 1 shows a configuration in which the biochemical module 110 is on the right side and the immune module 210 is on the left side of FIG. 1, but the automatic analyze system 100 may has a configuration in which a biochemical module is on the left side and an immune module is on the right side, or analyze devices on both sides are biochemical modules or analyze devices on both sides are immune modules. Further, three or more devices may be connected to the transport module 310, and it is desirable that at least two devices are connected to the transport module 310 in the invention.

In the transport module 310, a specimen rack 1 disposed in the specimen rack input unit 3 is transported to the specimen rack waiting disk 7 by the transport line 6. A specimen presence and absence determination sensor (not shown) is provided in an intermediate portion of the transport line 6, and the presence and absence of a specimen container 2 on the specimen rack 1 is recognized. If it is determined that the specimen container 2 is present here, the specimen and rack ID read unit 5 reads a specimen barcode (not shown) affixed on the specimen container 2 and recognizes identification information of the specimen container 2. In the actual automatic analyze system 100, a patient is specified by the identification information, and dispensing is scheduled by collating a request content of an inspection item with an upper host.

The specimen rack waiting disk 7 has a rotor structure that performs circular motion, and includes slots for radiatively holding a plurality of specimen racks 1 on a concentric circle on which a plurality of specimen containers 2 are placed on an outer circumference. By rotating these slots by a motor, any specimen rack 1 is carried in and out of a requested destination of the biochemical module 110 and the immune module 210. With such a structure, it is not necessary to process the specimen rack 1 placed first in order. In other words, if one specimen rack 1 has a high priority, the specimen rack 1 can be processed first.

The transport line 6 is connected to a certain point on the radial circumference of the specimen rack waiting disk 7, and the specimen rack 1 is carried in and out. When the point is at a position of 0 degree on the circumference, sampling lines 14, 20 for drawing the specimen rack 1 into the biochemical module 110 and the immune module 210, which will be described later, are connected at positions of 90 degrees on the circumference from the position where the transport line 6 is connected, and the specimen rack 1 is carried in and out.

As for which of the left and right analyze devices the specimen rack 1 will be transported to via the specimen rack waiting disk 7, the specimen rack 1 is first transported to the analyze device having a lighter load calculated based on loads of analysis items (test time×the number of test items).

The specimen rack 1 that has been dispensed in the biochemical module 110 and the immune module 210 waits for output of a measurement result in the specimen rack waiting disk 7, and processing such as automatic retesting can be performed if necessary. When the processing is ended, the specimen rack 1 is transported to the specimen rack housing unit 8 via the transport line 6.

The control unit for transport module 310a is a unit that controls an operation for transporting appropriate specimen racks 1 from the specimen rack waiting disk 7 to the sampling lines 14, 20 and a transport operation for returning the specimen rack 1 from the sampling lines 14, 20 to the specimen rack waiting disk 7, and controls an operation of each mechanism based on a command from the overall management computer 9, which will be described later.

The biochemical module 110 includes the sampling line 14, a specimen sampling mechanism 15, a reaction cell disk 16, a biochemical measurement unit 17 for measuring a physical property of a reaction solution, a reagent pipetting mechanism 18, a reagent disk 19, and a computer for biochemical module 13.

The specimen sampling mechanism 15 is rotatable and movable up and down, and moves to above the specimen container 2 placed on the specimen rack 1 transported by the sampling line 14. After that, the specimen sampling mechanism 15 descends and suctions a predetermined amount of the specimen held in the specimen container 2.

The specimen sampling mechanism 15 that suctions the specimen moves to above the reaction cell disk 16 and then descends to discharge the specimen into one of a plurality of reaction cells provided on the reaction cell disk 16. After dispensing the specimen into the reaction cell, the reaction cell disk 16 rotates and moves to a reagent dispensing position.

The reagent pipetting mechanism 18 is rotatable and movable up and down. After moving to above a reagent cassette in the reagent disk 19 in which the temperature is adjusted, the reagent pipetting mechanism 18 descends and suctions a predetermined amount of the reagent in the reagent cassette.

The reagent pipetting mechanism 18 moves to above the reaction cell disk 16 and then descends to discharge the reagent into the reaction cell in which the specimen is previously dispensed. The reaction cell disk 16 into which the reagent is discharged rotates and moves to a stirring position, and the specimen and the reagent are stirred by a stirring mechanism (not shown).

After stirring, the reaction cell disk 16 rotates and moves to a measurement position, and the biochemical measurement unit 17 measures optical characteristics and the like of the mixed solution in the reaction cell.

The computer for biochemical module 13 is a computer that controls operations required for analysis processing in the biochemical module 110, and controls the operation of each device in the biochemical module 110 based on a command from the overall management computer 9 described later.

In the biochemical module 110, specimen dispensing, reagent dispensing, stirring, and analysis can be performed in sequence and accordingly, specimen analysis can be executed in one sequence. Therefore, the biochemical module 110 can be scheduled at the timing of dispensing the specimen.

The immune module 210 includes the sampling line 20, a specimen sampling mechanism 21, an incubator disk 22, an immunoassay unit 23 for measuring a physical property of a reaction solution, a reagent pipetting mechanism 24, a reagent disk 25, a specimen dispensing tip and reaction container transport mechanism 26, a reaction solution suction nozzle 27, a transfer mechanism 32, a magnetic separate unit 34, and a computer for immune module 33.

A plurality of reaction containers for holding the reaction solution obtained by mixing and reacting the specimen and the reagent can be disposed on the incubator disk 22, and each of the reaction containers disposed in a circumferential direction can be rotated and move to a predetermined position. Unlike the reaction cells of the biochemical module 110, the reaction containers on the incubator disk 22 is disposable.

The specimen dispensing tip and reaction container transport mechanism 26 is movable in three directions of an X-axis, a Y-axis, and a Z-axis, and moves within a predetermined range of a specimen dispensing tip and reaction container holding member 28, a reaction container stirring mechanism 29, a specimen dispensing tip and reaction container disposal hole 30, a specimen dispensing tip mounting position 31, and the incubator disk 22 to transport specimen dispensing tips and the reaction containers.

A plurality of unused reaction containers and specimen dispensing tips are disposed on the specimen dispensing tip and reaction container holding member 28. The specimen dispensing tip and reaction container transport mechanism 26 moves to above the specimen dispensing tip and reaction container holding member 28, descends to grip an unused reaction container and then rises, and further moves to a predetermined position above the incubator disk 22 and descends to dispose the reaction container.

A plurality of reagent containers are disposed on the reagent disk 25. A reagent disk cover is provided on an upper portion of the reagent disk 25, and the inside of the reagent disk 25 is kept at a predetermined temperature. A reagent disk cover opening is provided in a part of the reagent disk cover.

The reagent pipetting mechanism 24 is rotatable and movable up and down, and rotates and moves to above the reagent disk cover opening, and then descends and immerses a tip end of the reagent pipetting mechanism 24 in a reagent in a predetermined reagent container to suction a predetermined amount of the reagent. Next, the reagent pipetting mechanism 24 ascends and then rotates and moves to the predetermined position above the incubator disk 22 to discharge the reagent into the reaction container.

The specimen dispensing tip and reaction container transport mechanism 26 moves to above the specimen dispensing tip and reaction container holding member 28, descends to grip an unused specimen dispensing tip and then rises, and further moves to above the specimen dispensing tip mounting position 31 and descends to dispose the specimen dispensing tip.

The specimen sampling mechanism 21 is rotatable and movable up and down, and rotates and moves to above the specimen dispensing tip mounting position 31 and then descends, so that the specimen dispensing tip is mounted on the tip end by press-fitting. The specimen sampling mechanism 21 on which the specimen dispensing tip is mounted moves to above the specimen container 2 placed on the specimen rack 1 and then descends to suction a predetermined amount of the specimen held in the specimen container 2 transported by the sampling line 20.

The specimen sampling mechanism 21 that suctions the specimen moves to above the incubator disk 22 and then descends to discharge the specimen into the reaction container into which the reagent is previously discharged.

When the specimen discharge is completed, the specimen sampling mechanism 21 moves to above the specimen dispensing tip and reaction container disposal hole 30, and the used specimen dispensing tip is discarded.

The reaction container into which the specimen and the reagent are discharged is moved to a predetermined position by the rotation of the incubator disk 22, and is transported to the reaction container stirring mechanism 29 by the specimen dispensing tip and reaction container holding member 28. The reaction container stirring mechanism 29 stirs and mixes the specimen and the reagent in the reaction container by applying a rotation motion to the reaction container. The reaction container after stirring is returned to the predetermined position of the incubator disk 22 by the specimen dispensing tip and reaction container holding member 28.

After the reaction between the specimen and the reagent is started by stirring, another reagent may be further added at a specific timing to perform the reaction. For example, there is a process of further binding a magnetic bead having an antibody bound to its surface to the antigen. Therefore, the reaction container placed on the incubator disk 22 for predetermined time is transported to the magnetic separate unit 34 by the transfer mechanism 32, and magnetic separation processing is performed on the specimen. After the magnetic separation processing is completed, the reaction container is transported to the incubator disk 22 again by the transfer mechanism 32.

Regardless of the presence or absence of magnetic separation, the reaction container that has been placed on the incubator disk 22 for the predetermined time is transported to directly below the reaction solution suction nozzle 27 by the transfer mechanism 32, and the reaction solution is guided to the immunoassay unit 23 by the reaction solution suction nozzle 27.

The immunoassay unit 23 detects a signal from the reaction solution, outputs the signal to the overall management computer 9, notifies the user of an analysis result, and records the analysis result in a memory unit 9a.

The reaction container from which the reaction solution is suctioned returns to the incubator disk 22 by the transfer mechanism 32. After that, the reaction container is moved to a predetermined position by the rotation of the incubator disk 22, moved from the incubator disk 22 to above the specimen dispensing tip and reaction container disposal hole 30 by the specimen dispensing tip and reaction container holding member 28, and discarded.

The computer for immune module 33 is a computer that controls operations required for analysis processing in the immune module 210, and controls the operation of each device in the immune module 210 based on a command from the overall management computer 9 described later.

Since the plurality of reaction containers can be disposed in the incubator disk 22, the reaction itself in the immune module 210 can proceed at the same time. However, in the device, even if there is only one measurement unit and a plurality of measurement sequences, measurement time is longer than those for operations of the other mechanical parts. Since there is no overlapping use of and operation interference with the other mechanical parts, scheduling is performed centering on the immunoassay unit 23.

FIG. 2 is a functional block diagram showing functions of the overall management computer 9 from scheduling of the specimen analysis to analysis execution.

The overall management computer 9 is a unit that plays a role of controlling information of units of the entire automatic analyze system 100, and as shown in FIGS. 1 and 2, includes a request input unit 101, a rack management unit 102, a planning unit 103, a request analyze unit 104, a mechanism control unit 105, a result output unit 106, the memory unit 9a, and an arithmetic processing unit 9b.

The overall management computer 9 is connected to the biochemical module 110, the immune module 210, and the transport module 310 by a wired or wireless network line, and is further connected to an operation unit 10 for inputting necessary information, a display unit 11 for displaying an analysis result, and an external network 12.

The memory unit 9a is a unit that stores time charts and operation parameters required for operations in the automatic analyze system 100, various information for specifying a specimen, a measurement result, or the like, and is implemented by a storage medium, for example, a semiconductor memory such as a flash memory or a magnetic disk such as an HDD.

The arithmetic processing unit 9b calculates a concentration of a specific component in a measurement target based on measurement results in the biochemical measurement unit 17 of the biochemical module 110 and the immunoassay unit 23 of the immune module 210.

The request input unit 101 has a function of receiving a measurement request, which is requested by a doctor or the like to measure a certain specimen by the biochemical module 110 or the immune module 210, from a laboratory information system (LIS), a hospital information system (HIS), the operation unit 10, or the like.

The rack management unit 102 collates a rack ID and a specimen ID read by the specimen and rack ID read unit 5 with the measurement request from the request input unit 101, and manages the measurement request for the specimen on the specimen rack 1.

The planning unit 103 plans a measurement schedule of the specimen requested to be executed by the biochemical measurement unit 17 of the biochemical module 110 and the immunoassay unit 23 of the immune module 210.

Here, in the present embodiment, the measurement in the immunoassay unit 23 includes items having different measurement times. In view of such circumstances, in the planning unit 103 of the present embodiment, in particular, when an item of a sequence having the longest measurement time is continuously measured for a predetermined number of times or more, for example, at least twice, at least one free cycle is provided after the predetermined number of times or more of measurement.

Then, the planning unit 103 interrupts the free cycle with the measurement of an item of a sequence having a short measurement time when the item of the sequence having a short measurement time is requested.

The request analyze unit 104 calculates loads of the immune module 210 and the biochemical module 110 based on analysis time and the number of request items, and plans a transport schedule for the control unit for transport module 310a so that a rack is transported first to the analyze device having a lighter load.

For example, in the request analyze unit 104 of the present embodiment, of two or more biochemical modules 110 and immune modules 210, the specimen is scheduled to be preferentially transported to the side (basically, the immune module 210) having a lighter load obtained by multiplying the measurement time by the number of measurement items.

Further, the request analyze unit 104 performs scheduling such that when a plurality of measurement items are requested for the same specimen, waiting time at a dispensing position in the immune module 210 having a lighter load is long, and when the dispensing of the same specimen in the biochemical module 110 is delayed, the specimen is transported to the biochemical module 110 first regardless of the load.

Details of scheduling in the planning unit 103 and the request analyze unit 104 will be described later.

The mechanism control unit 105 operates mechanisms in the transport module 310 according to the measurement schedule scheduled by the planning unit 103 and the transport schedule scheduled by the request analyze unit 104, and also outputs a time chart for analysis operation to the computer for biochemical module 13 and the computer for immune module 33.

The result output unit 106 executes various output processing such as displaying the measurement result corresponding to the measurement request on the display unit 11, storing the measurement result in the memory unit 9a, and notifying LIS and HIS via the external network 12.

Mechanisms in the overall management computer 9 may be implemented by a general-purpose computer or as a function of a program executed on the computer.

That is, processing of the mechanisms in the overall management computer 9 may be implemented by storing the processing as program codes into a recording unit such as a memory and executing the program codes by a processor such as a central processing unit (CPU).

The mechanisms in the overall management computer 9 may be implemented by hardware such as a dedicated circuit board.

Returning to FIG. 1, the display unit 11 is a unit on which various screens such as an operation screen for ordering measurement items to be measured for a specimen to be measured, a screen for confirming a measurement result, or the like are displayed, and is implemented by a liquid crystal display or the like. The display unit 11 may not be a liquid crystal display, and may be replaced with a printer or the like, or may be a display and a printer.

In the present embodiment, in particular, there is provided a rack handling setting screen 11a or the like including a setting area 11b for setting a predetermined number of times as a reference for providing the free cycle.

The operation unit 10 is a unit for inputting various parameters and settings, measurement results, measurement request information, analysis start and stop instructions, or the like based on the operation screen displayed on the display unit 11, and is implemented by a keyboard, a mouse, or the like.

Next, details of a specimen analysis schedule in the automatic analyze system 100 according to the present embodiment will be described with reference to FIG. 3 and later. First, specific examples of requests for a general specimen and an emergency specimen, a transport destination analyze device, and the order of dispensing will be described with reference to FIGS. 3 to 5.

FIG. 3 is a diagram showing an outline of a specimen rack, and FIGS. 4 and 5 are explanatory diagrams showing an example of a rack transport destination for an analyze request item.

As shown in FIG. 3, the specimen rack 1 is equipped with a total of five specimen containers 2A, 2B, 2C, 2D, and 2E containing specimens, and a case where the following analysis requests are made is considered.

Biochemical analysis items C1, C2, C3 are requested for a specimen S1 contained in the specimen container 2A. The biochemical analysis item C1, an immunological analysis item having a normal priority E1, and an immunological analysis item having a high priority $E2^H$ are requested for a specimen S2 contained in the specimen container 2B. The biochemical analysis item C1 and the immunological analysis item having a high priority $E2^H$ are requested for a specimen S3 contained in the specimen container 2C. The biochemical analysis items C1, C3 are requested for a specimen S4 contained in the specimen container 2D. It is assumed that the biochemical analysis items C2, C3 and the immunological analysis item having a normal priority E1 are requested for a specimen S5 contained in the specimen container 2E.

Accordingly, both biochemical and immunological items can exist for one specimen container. In this case, when the request analyze unit 104 plans to first transport the specimen rack 1 to which analyze device, the specimen rack 1 is first transported to the analyze device having a lighter load calculated based on the loads of the analysis items (test time×the number of test items).

For example, when it is determined that the biochemical module 110 has a lighter load of the analysis items, the specimen rack 1 is first transported to the biochemical module 110 as shown in FIG. 4. Here, specimen dispensing is not performed for the specimen S2 and the specimen S3 for which the item of immunity having a high priority is set, and is performed only for the biochemical items (the items C1, C2, C3 for the specimen S1, the items C1, C3 for the specimen S4, the items C2, C3 for the specimen S5) of the specimens S1, S4, S5 for which the item of immunity having a high priority is not set.

Next, the specimen rack 1 is transported to the immune module 210, and the specimen S2 (E1, E2$^H$), the specimen S3 (E2$^H$), and the specimen S5 (E1) are dispensed for the items of immunity. After that, the specimen rack 1 is transported to the biochemical module 110 again, and specimen dispensing is performed for the biochemical item (S2 (C1), S3 (C1)) of the specimens (the specimen S2, the specimen S3) that could not be dispensed since the item of immunity having a high priority is set earlier.

Further, when it is determined that the immune module 210 has a lighter load of the analysis items, as shown in FIG. 5, dispensing is first performed only for the items of immunity (the item E1 and the item E2$^H$ for the specimen S2, S3 (E2$^H$), and S5 (E1)) in the immune module 210. After that, the specimen rack 1 is transported to the biochemical module 110, and dispensing is performed for the biochemical items (C1, C2, C3 for the specimen S1, the item C1 for the specimen S2, the item C1 for the specimen S3, the items C1, C3 for the specimen S4, and the items C2, C3 for the specimen S5).

Accordingly, the specimen rack 1 moves back and forth between the biochemical module 110 and the immune module 210 via the specimen rack waiting disk 7 depending on a request content of the inspection item.

Here, when there are items having different measurement times in the immunoassay unit 23 of the immune module 210 in the present embodiment, for example, when there is a 9-minute item after an 18-minute item, the specimen of the 18-minute item may come first, and waiting time for dispensing may occur at the dispensing position in the immune module 210, and the biochemical analysis item may be delayed.

Accordingly, even when it is determined that the immune module 210 has a load lighter than the biochemical module 110 and the specimen rack 1 is first transported to the immune module 210, time required to transport the specimen rack 1 to the biochemical module 110 will be extended, and thus there is a room for improvement in the turnaround time.

FIGS. 6 to 9 show a dispensing timing after continuously measuring the sequence A (18-minute item) having a long reaction time in the schedule centering on the immunoassay unit 23, and a dispensing timing when a free cycle is set.

As shown in FIG. 6, when an item in the sequence B (9 minutes) having a short reaction time is requested, dispensing can be performed immediately if the schedule after 9 minutes of the measurement cell is available.

However, as shown in FIG. 7, when items in the sequence A (18 minutes) having a long measurement time are scheduled continuously, the schedule of measurement cells is filled for 18 minutes, and the specimen rack 1 will wait at a dispensing position for up to 9 minutes. Therefore, even in a measurement sequence in which the measurement result can be obtained by a reaction of 9 minutes, the turnaround time may be 18 minutes.

In contrast, according to the control of the invention, when the sequence A (18 minutes) having a long reaction time is continuously analyzed, at least one free cycle is provided after performing a specified number of times of continuous measurement. As shown in FIG. 8, for the sequence A having a long reaction time, the turnaround time is slightly longer because the measurement is performed after the free cycle has elapsed.

However, as shown in FIG. 9, since measurement of a short sequence can be performed by interrupting measurement of a long sequence, the waiting time at the dispensing position is short, and an analysis of an STAT specimen can be performed more quickly than in FIGS. 6 and 7.

In particular, when only one measurement unit is disposed in the automatic analyze system or the automatic analyze device, even if there are a plurality of measurement sequences, the measurement time is longer than those of operations of other mechanical parts, and it is almost unnecessary to consider the overlapping use of and the operation interference with the other mechanical parts. Therefore, the scheduling is performed centering one the measurement unit and a short sequence can be reliably interrupted with by making one free cycle.

On the other hand, as in the present embodiment, when there are a plurality of measurement units (the biochemical measurement unit 17 and the immunoassay unit 23) in the system, it is necessary to consider the overlapping use of and the operation interference with the other mechanical parts, and it may not be possible to interrupt with a short sequence by only one free cycle.

FIGS. 12, 13, and 14 show results of verifying the turnaround time when 50 general specimens as shown in FIG. 10 and one emergency specimen as shown in FIG. 11 are branched. FIG. 12 shows an example of turnaround time of the STAT (emergency) specimen when no free cycle is set as in an automatic analyze system in the related art. FIG. 13 shows an example of turnaround time of the STAT (emergency) specimen when the free cycle is set to once every five times. FIG. 14 shows an example of turnaround time of the STAT (emergency) specimen when the free cycle is set to once every ten times.

As shown in FIG. 10, general specimens in the specimen containers at positions 1 to 5 are analyzed for a 10-minute biochemical item by three times, an ISE item once, and an 18-minute immunological item once, and 50 specimens (10 racks) are disposed in a state where the specimen rack 1 for 5 containers is filled with the specimen containers 2 from the 1st to 5th positions. Therefore, a total number of times of analysis is 150 for the biochemical item and the ISE item, and 50 for the immunological item.

The ISE item is an item for measuring concentrations of electrolytes (Na, K, Cl ions) in a specimen, which is mostly disposed in the biochemical module 110 among the modules shown in FIG. 1. In the present embodiment, the illustration is omitted for convenience of description.

As shown in FIG. 11, one rack is disposed in a state in which only one specimen container 2 containing the emergency specimen for a 10-minute biochemical item by 14 times, an ISE item once, and a 9-minute immunological item by twice is disposed in the position 1 only, and the 2nd to 5th positions are available. Therefore, a total number of times of analysis is 14 for the biochemical item, 3 for the ISE item, and 2 for the immunological item.

As shown in FIG. 12, in a case of no free cycle in the related art, the turnaround time of the specimens Nos. 1 to 40 among the general specimens was almost constant. However, the turnaround time is delayed because the STAT specimen interrupted in the specimens Nos. 41 to 50.

In particular, even though the immunological item is a 9-minute sequence item, the No. 51 STAT specimen, which requires a short turnaround time, has already been requested for the 18-minute sequence item of the previous general specimen in succession, and thus there is no free cycle in the schedule of the measurement unit. Therefore, there is a limit to interrupting a general specimen, a schedule of the 9-minute sequence item is established after 9 minutes, and the specimen will wait for 9 minutes at the dispensing position. As a result, the turnaround time is 1326 seconds (about 22 minutes).

In contrast, as shown in FIG. 13, among the immunological items, the 18-minute sequence is performed for 5 times continuously and then one free cycle is inserted. At this time, the specimens from No. 6 on among the general specimens are interrupted with the free cycle, and accordingly the turnaround time is slightly delayed every 5 specimens.

However, the No. 51 STAT specimen which requires a short turnaround time can be measured by interruption with a free cycle prepared every 5 cycles. Therefore, the turnaround time is 974 seconds (about 16 minutes), and it can be seen that the turnaround time can be improved by about 6 minutes compared to the case where no free cycle is set.

Under conditions shown in FIG. 11 in the present embodiment, two 9-minute sequence items of the STAT specimen are set, and thus the improvement is about 6 minutes. However, when only one item is set, the turnaround time is improved by about 9 minutes.

As shown in FIG. 14, when the 18-minute sequence is performed for 10 times continuously and then one free cycle is inserted, it is the same as when the free cycle is set once every 5 cycles, and the turnaround time of the general specimens is delayed. However, the turnaround time of highly emergency STAT specimens can be shortened from 1372 seconds (about 22 minutes) to 1080 seconds (18 minutes) compared to the case where no free cycle is set.

As shown in FIGS. 12, 13, and 14, when there is no STAT specimen (or 9-minute sequence item), a total performance will drop by about 20% when simply one free cycle is set every 5 cycles and by about 10% when one free cycle is set every 10 cycles. However, when comparing the case where there is the STAT specimen, it is possible to perform the measurement with almost no decrease in the total performance because a short sequence can be inserted in the free cycle.

FIG. 15 is a diagram showing a processing flow of the planning unit 103 of the overall management computer 9. The following steps are executed by the planning unit 103.

First, the planning unit 103 receives an analysis request from the rack management unit 102 (step S201).

After that, the planning unit 103 determines whether a sequence of the received request is the sequence A having a long reaction time or the sequence B having a short reaction time (step S202). When the sequence is the sequence A having a long reaction time, the processing proceeds to step S203.

Next, the planning unit 103 determines whether a cumulative number of times of measurement in the sequence A is equal to or larger than a set value (step S203). When it is determined that the cumulative number is equal to or larger than the set value, the processing proceeds to step S204. In contrast, when it is determined that the cumulative number is smaller than the set value, the processing proceeds to step S206.

After that, the planning unit 103 inserts a free cycle (step S204), rewrites the cumulative number of times of the measurement in the sequence A to 0 (step S205), and starts the measurement.

In contrast, when it is determined that the cumulative number of times of the measurement in the sequence A does not exceed the set value, the cumulative number of times of the measurement in the sequence A is added by 1 (step S206), and the processing proceeds to step S207.

When it is determined in step S202 that the sequence is the sequence B having a short reaction time, after the cumulative number of times of the measurement in the sequence A is added by 1, sequence allocation is performed (step S207), and the measurement is started.

After that, the planning unit 103 determines whether all the received requests are processed (step S208). When it is determined that all the requests are processed, the processing is ended. In contrast, when it is determined that not all the requests are processed, the processing is returned to step S202, and the processing is repeated until the schedule of all the requests is ended.

FIG. 16 shows an example of a rack handling setting screen.

In the automatic analyze system 100 of the present embodiment, the rack handling setting screen 11a including the setting area 11b for setting a predetermined number of times as a reference for providing the free cycle can be displayed on the display unit 11. In the setting area 11b, a manual selection area 11c is selected, and the predetermined number of times is set for at least one of each day of a week and each date and time.

For this purpose, the planning unit 103 causes the rack handling setting screen 11a of the display unit 11 to display the setting area 11b as shown in FIG. 16. In the setting area 11b, the number of free cycles (once every 0 to 17 times or automatic setting) can be selected for the STAT specimen for each day of a week and each date and time. The value is input by, for example, the operation unit 10.

In the case of the present embodiment, the analysis is performed in a 30-second cycle, and a free cycle 18 is obtained by 9 minutes÷30 seconds=18, which is equivalent to the maximum waiting time of 9 minutes. Therefore, it is possible to set the number of times as 0 to 17, and even if the analysis cycle time changes and a range in which the free cycle can be set increases to 17 or more, the setting of the free cycle may be displayed as a ratio from the number of times that the specimen can be continuously dispensed.

Further, the number of times may be set to be finer than each day of a week and each date and time, or be uniform conversely.

In FIG. 16, by selecting an OK button 11e by operating the operation unit 10, the planning unit 103 performs scheduling to provide a free cycle when measurement of a sequence having a long measurement time is continuously performed for the number of times input to the setting area 11b.

When a cancel button 11f is selected, the free cycle is set not based on the number of times input to the setting area 11b, but is set based on the previous setting.

Further, in the present embodiment, the display unit 11 can display an area for setting the number of available positions (0 to 20 or automatic setting) of the specimen rack waiting disk 7.

This is because when no available position dedicated to an emergency specimen is prepared, the specimen rack waiting disk 7 may be full and it may be not possible to request for an interruption with another specimen even if an there is an emergency specimen rack. Therefore, when a free cycle is set, it is desirable to prepare at least one available position on the specimen rack waiting disk 7 at the same time as the setting.

By performing the above setting and creating a free cycle and an available position on the specimen rack waiting disk 7, in the measurement of the STAT item, the free cycle and the available position on the specimen rack waiting disk 7 can be used to shorten waiting time for starting the measurement.

FIG. 17 is a diagram showing a method for automatically calculating the setting of the free cycle.

When an automatic selection area 11d is selected on the rack handling setting screen 11a of FIG. 16, the planning unit 103 automatically sets a free cycle based on the following calculation contents.

For example, FIG. 17 considers a case in which the number of requests for both the 18-minute item and the 9-minute item is larger on Monday morning than other time and days of the week, or in which the number of requests in the morning is larger than that in the afternoon on each day of the week.

Based on the number of measurement items for the past 9 weeks, the planning unit 103 obtains the number of items in the sequence A having a long reaction time and the sequence B having a short reaction time for each date and time (per hour) and each day of a week, and calculates an average value and a standard deviation SD.

After that, the planning unit 103 deletes data outside a range of the average value±3×SD, calculates an average value and a standard deviation based on the deleted data, and obtains a range of the average value±2×SD as a standard range. Accordingly, an average number of items in the sequence A per hour (referred to as A), an average number of items in the sequence B per hour (referred to as B), and an average number of times of measurement per hour (referred to as X) are obtained (A+B≈X).

A case where an average operation rate per hour is 50% or more (X/Y>0.5) with respect to a processing capacity per hour (Y) of the analyze device is considered. In this case, since there is less free cycles in the scheduling of the measurement unit with respect to the processing capacity of the device, a value obtained by taking the reciprocal of a ratio (B/X) occupied by the average number of items in the sequence B per hour (rounded up to an integer) is determined as the free cycles.

Further, when the ratio (B/X) of the average number of items in the sequence B per hour is less than 10%, since it can be determined that a request for measuring the sequence B is not so high and it is not necessary to provide free cycles frequently, the free cycle is set to 10.

Furthermore, when the ratio (B/X) of the average number of items in the sequence B is 50% or more, it is necessary to provide free cycles frequently so that the free cycle is set to 2.

Here, the free cycle can be set from 0 to 17, but when the free cycle is set to 17, the waiting time at the dispensing position will be about 8 minutes in a worst case. Therefore, it is desirable to use 0 to 10 for the automatic setting.

Further, when the ratio (B/X) of the average number of items in the sequence B per hour is used, the above calculation may be performed by substituting either an upper limit or a lower limit in the standard range of the average value±2SD.

Further, it is assumed that when the average operation rate per hour is 50% or less (X/Y<0.5) with respect to the processing capacity per hour (Y) of the analyze device, there are sufficient free cycles in the scheduling of the measurement unit. There are multiple free cycles in scheduling, and free cycles for interruption with emergency specimens are originally secured at a certain level. Therefore, it is desirable to set the free cycle to 10.

Further, when the ratio (B/X) of the average number of items in the sequence B per hour is 0, it is rarely necessary to have a free cycle for items in a sequence having a short measurement time. Therefore, it is desirable to set the free cycle to 0. This is a setting suitable for the operation of, for example, an inspection center that analyzes a specimen such as a health examination with low emergency.

In addition to the above calculation, an average value or maximum and minimum ratios may be simply used.

Further, when the ratio of emergency specimens varies widely and the calculation is not suitable for an actual operation, as shown in FIG. 16, the free cycle may be manually input to a specific day of a week and time zone, and the setting can be automatically switched. Switching is performed by selecting the manual selection area 11c or the automatic selection area 11d on the rack handling setting screen 11a.

Next, effects of the present embodiment will be described.

The automatic analyze system 100 of the present embodiment described above includes the biochemical module 110 and the immune module 210 for analyzing at least one specimen, and the transport module 310 for supplying the specimen to the biochemical module 110 and the immune module 210. The automatic analyze system 100 includes the incubator disk 22 including a plurality of reaction containers which hold a reaction solution obtained by mixing and reacting of a specimen with a reagent, the immunoassay unit 23 which measures a physical property of the reaction solution, and the planning unit 103 which determines an order of measurement of the specimen requested to be executed by the immunoassay unit 23. The measurement in the immunoassay unit 23 includes items with different measurement times. The planning unit 103 performs at least one free cycle after the measurement of the predetermined number of times or more when continuously measuring an item of a sequence having the longest measurement time for at least two or more predetermined times or more.

Accordingly, when a sequence having a long reaction time is continuously analyzed, by providing at least one free cycle after performing a specified number of times of continuous measurement, it is possible to interrupt the long sequence with measurement of a short sequence. Therefore, it is possible to use a free cycle in measurement of an STAT item, and it is possible to shorten the waiting time for starting the measurement. Further, even if at least one free cycle is provided, the turnaround time of a general specimen does not deteriorate fairly, which contributes to the improvement of a total turnaround time.

In particular, the STAT item which requires a short reaction time is an analysis item used in emergency specimen measurement or the like, and there is always a need for a short turnaround time. Therefore, in large hospitals, there are daily cases where emergency specimens are measured during routine measurement. In such a case, by executing the measurement schedule control of the invention, the turnaround time of the STAT item can be shortened, which can contribute to early diagnosis.

Further, when an item in a sequence having a short measurement time is requested, since the planning unit 103 interrupts the free cycle with the measurement of the item of the sequence having a short measurement time, it is possible to reliably perform an interruption with the STAT item and perform measurement at an early stage.

Furthermore, by further providing the setting area 11b for setting a predetermined number of times for providing the free cycle, it is possible to set a free cycle according to an operation location of the system. Therefore, it is possible to create a more flexible measurement plan, and it is possible to more reliably prevent deterioration of the turnaround time.

Further, the setting area 11b can manually set the predetermined number of times for at least each day of a week or for each date and time. Therefore, for example, in a facility, a day of a week, or a time zone where there is no measurement request for a short sequence, it is possible to prevent turnaround time of a measurement request for a long sequence from being dropped by creating no free cycle. At the same time, when there are many measurement requests for short sequences, the free cycle can be positively provided, and the turnaround time can be further improved.

Further, the planning unit 103 calculates a ratio of the measurement of the specimen in the sequence having a short measurement time for each date and time or each day of a week based on a past measurement status of the immune module 210, and automatically sets a predetermined number of times for providing the free cycle. Therefore, the planning unit 103 can determine a ratio according to an analysis status based on the past cumulation, for example, the ratio of free cycles is increased because the number of requests is large and a ratio of emergency specimens is large on Monday morning, and the ratio of free cycles is decreased because the ratio of emergency specimens is large but the number of requests per hour is small on Monday afternoon. Further, at an inspection center where a ratio of emergency specimens is low, the free cycle is zero, and it is possible to prevent turnaround time of a general specimen from decreasing by creating a free cycle unnecessarily.

Further, a manual setting of a predetermined number of times by the setting area 11b and an automatic setting of a predetermined number of times by the planning unit 103 can be switched. Therefore, a free cycle can be set according to the operating status of the automatic analyze system 100, which can reliably contribute to the improvement of the turnaround time.

Furthermore, when the biochemical module 110 and the immune module 210 are separately connected to the transport module 310 and analyze different measurement items, even when items with different measurement sequences are mixed as described above, the device configuration can greatly receive a merit of preventing turnaround time of measurement from becoming fairly deteriorated.

Further, of two or more biochemical modules 110 and immune modules 210, a specimen is preferentially transported to the immune module 210 having a lighter load obtained by multiplying the measurement time by the number of measurement items. Therefore, the measurement can be performed at an early stage and the turnaround time can be improved.

Furthermore, when a plurality of measurement items in the biochemical module 110 and the immune modules 210 are requested for the same specimen, the waiting time at the dispensing position in the immune module 210 having a lighter load is long, and when the dispensing of the same specimen in the biochemical module 110 is delayed, the specimen is first transported to the biochemical module 110 regardless of the load, and thus deterioration of the turnaround time can prevented more reliably.

Other Embodiments

The invention is not limited to the above embodiment, and various modifications and applications can be made thereto. For example, the above-described embodiment has been described in detail in order to make the invention easy to understand, and the invention is not necessarily limited to those which have all the configurations described.

For example, in the above-described embodiment, the case where at least one free cycle is provided after the measurement of a predetermined number of times or more has been described, and two or more free cycles may be provided. Such a setting is considered to be particularly effective for an automatic analyze system operated in a place where, for example, the number of request items for one emergency specimen is large or an input ratio of the emergency specimen is fairly large.

REFERENCE SIGN LIST 1 specimen rack
2, 2A, 2B, 2C, 2D, 2E specimen container
3 specimen rack input unit
4 emergency specimen container input unit
5 specimen and rack ID read unit
6 transport line
7 specimen rack waiting disc
8 specimen rack housing unit
9 overall management computer
9a memory unit
9b arithmetic processing unit
10 operation unit
11 display unit
11a rack handling setting screen
11b setting area (setting unit)
11c manual selection area
11d automatic selection area
11e OK button
11f cancel button
12 external network
13 computer for biochemical module
14 sampling line
15 specimen sampling mechanism
16 reaction cell disc
17 biochemical measurement unit
18 reagent pipetting mechanism
19 reagent disk
20 sampling line
21 specimen sampling mechanism
22 incubator disk
23 immunoassay unit
24 reagent pipetting mechanism
25 reagent disk
26 reaction container transport mechanism 27 reaction solution suction nozzle
28 reaction vessel holding member
29 reaction vessel stirring mechanism
30 specimen dispensing tip and reaction container disposal hole
31 specimen dispensing tip mounting position
32 transfer mechanism
33 computer for immune module
34 magnetic separate unit
100 automatic analyze system
101 request input unit
102 rack management unit
103 planning unit
104 request analyze unit
105 mechanism control unit
106 result output unit
110 biochemical module (automatic analyze device)
210 immune module (automatic analyze device)
310 transport module (transport device)
310a control unit for transport module

The invention claimed is:

1. An automatic analyze system which analyzes a specimen, comprising:
   at least two automatic analyze devices operating in conjunction and which are individually connected to two or more transport devices and analyze measurement items which are different from each other;
   a transport device which supplies the specimen to the at least two automatic analyze devices, the transport device including a transport line and specimen rack waiting disk; and
   a processor, a memory, and a storage in communication with the at least two automatic analyze devices and the transport device,
   wherein the automatic analyze system further includes:
      an incubator which is equipped with a plurality of reaction containers which hold reaction solution obtained by mixing and reacting the specimen with a reagent;
      a detection circuit which measures a physical property of the reaction solution; and
      a planning circuit which determines an order of a measurement of the specimen requested to be executed on the detection circuit,
   the measurement in the detection circuit includes items with different measurement times,
   the planning circuit provides at least one free cycle after the measurement of at least a predetermined number of times which is at least two, when continuously measuring an item of a sequence with the longest measurement time for at least the predetermined number of times,
   the specimen is preferentially transported to a one of the at least two automatic analyze devices with a light load obtained by multiplying measurement time by a number of measurement items among the two or more sets of the automatic analyze devices, and
   when the measurement item in the plurality of automatic analyze devices on the same specimen is requested, a waiting time is long at a dispensing position in the automatic analyze device on the side with the light load, and when dispensing in the other automatic analyze device of the same specimen is delayed, the specimen is transported to the other automatic analyze device first regardless of the load.

2. The automatic analyze system according to claim 1, wherein
   the planning circuit is further configured to interrupt in the measurement of an item of a sequence with a short measurement time in the free cycle when the item of the sequence with the short measurement time is requested.

3. The automatic analyze system according to claim 2, further comprising:
   a setting circuit which sets the predetermined number of times for provision of the free cycle.

4. The automatic analyze system according to claim 3, wherein
   the setting circuit is capable of manually setting the predetermined number of times to at least one of each day of a week, and each date and time.

5. The automatic analyze system according to claim 3, wherein
   the planning circuit calculates a ratio of the measurement of the specimen in the sequence with the short measurement time for each date and time or each day of a week from a past measurement status of the automatic analyze device, and automatically sets the predetermined number of times to provide the free cycle.

6. The automatic analyze system according to claim 5, wherein
   the manual setting of the predetermined number of times by the setting circuit and the automatic setting of the predetermined number of times by the planning circuit are switchable.

\* \* \* \* \*